US006749842B2

(12) United States Patent
Miller et al.

(10) Patent No.: US 6,749,842 B2
(45) Date of Patent: Jun. 15, 2004

(54) LIQUID FOAM BUILDER CONTAINING HYDROLYZED GRAIN PROTEIN

(75) Inventors: Jeremy T. Miller, Kansas City, MO (US); Clodualdo C. Maningat, Platte City, MO (US); Sukh Bassi, Atchison, KS (US); Dharmen Makwana, Platte City, MO (US); Rangaswamy Chinnaswamy, Kansas City, MO (US)

(73) Assignee: Midwest Grain Products, Atchison, KS (US)

( * ) Notice: Subject to any disclaimer, the term of this patent is extended or adjusted under 35 U.S.C. 154(b) by 0 days.

(21) Appl. No.: 10/057,215

(22) Filed: Jan. 24, 2002

(65) Prior Publication Data

US 2003/0138391 A1 Jul. 24, 2003

(51) Int. Cl.$^7$ .......................... A61K 7/075; A61K 9/00
(52) U.S. Cl. ...................................... 424/70.19; 424/400
(58) Field of Search ............................ 424/70.19, 400

(56) References Cited

U.S. PATENT DOCUMENTS

| 3,814,816 | A | * | 6/1974 | Gunther ........................ 426/46 |
| 3,972,998 | A | * | 8/1976 | Keiner ....................... 424/70.16 |
| 4,390,450 | A | * | 6/1983 | Gibson et al. ................. 516/16 |

* cited by examiner

Primary Examiner—Christopher R. Tate
Assistant Examiner—Kailash C. Srivastava
(74) Attorney, Agent, or Firm—Hovey Williams LLP

(57) ABSTRACT

Improved liquid foamer products, methods of preparation thereof, and end-use personal care products including the foamers are provided wherein the liquid foamers comprise a quantity of aqueous liquid hydrolyzed grain protein (e.g., aqueous liquid hydrolyzed wheat gluten protein) with an amount up to about 10% by weight of initially solid hydrolyzed grain protein (e.g., hydrolyzed wheat gluten protein powder) solubilized in the liquid ingredient. The foamer products have good foaming and color characteristics, and can be readily incorporated into a variety of personal care product formulations.

26 Claims, No Drawings

US 6,749,842 B2

LIQUID FOAM BUILDER CONTAINING HYDROLYZED GRAIN PROTEIN

BACKGROUND OF THE INVENTION

1. Field of the Invention

The present invention is broadly concerned with improved foamer products designed for use in personal care products such as shampoos and the like. More particularly, the invention pertains to foamer products, methods of preparation thereof and personal care products including the foamers, wherein the roamer products include a quantity of an aqueous liquid hydrolyzed grain protein such as aqueous hydrolyzed wheat gluten protein, with an amount of initially solid hydrolyzed grain protein solubilized in the liquid ingredient. Such foamer products can be readily incorporated into personal care items and have good foaming properties.

2. Description of the Prior Art

A number of liquid products are designed to generate foam upon use thereof. For example, personal care products such as shampoos and bath and shower gels must noticeably foam in order to be acceptable to consumers. Similarly, detergents and other types of cleaning products also must foam. In the past, a large number of foaming agents have been used in these types of products. The goal is to create an acceptable amount of foam without over-foaming.

In recent years, the consuming public has evinced considerable interest in so-called "all-natural" personal care products, as opposed to those containing synthetic ingredients perceived to be less desirable. In the case of foaming agents, it has been known to provide hydrolyzed wheat gluten protein powder as a foaming agent. While this material is deemed "natural", and generally has acceptable foaming properties, it is often very difficult to readily solubilize or disperse the powder during formulation. If conventional blending and mixing techniques are followed, quantities of the powder settle out and/or create a hazy, unacceptable appearance. Thus, compounders have been forced to employ specialized equipment or processing steps in order to use hydrolyzed wheat gluten protein foaming agents.

Aqueous liquid hydrolyzed wheat gluten protein has also been available, but has not found any utility as a foaming agent. Indeed, such liquids simply do not have any real degree of foam-generating power.

There is accordingly a need in the art for an improved hydrolyzed grain protein foaming agent which has good foaming properties while at the same time being readily usable in various product formulations without the need for specialized mixing steps or equipment.

SUMMARY OF THE INVENTION

The present invention overcomes the problems outlined above, and provides an improved liquid foamer product broadly including a quantity of aqueous liquid hydrolyzed grain protein, together with an amount up to about 10% by weight of initially solid hydrolyzed grain protein solubilized in the liquid hydrolyzed grain protein. It has been found that such a combination retains the good foaming characteristics of the initially solid product, while overcoming the formulation problems inherent in the use thereof.

In more detail, the liquid and initially solid hydrolyzed grain protein ingredients are preferably selected from the group consisting of proteins derived from wheat gluten, soy, rice, oat, corn, jojoba and mixtures thereof, and advantageously the liquid and solid protein ingredients are both prepared from the same natural protein. In practice, it is preferred that both the liquid and solid ingredients be hydrolyzed wheat gluten protein.

The overall foamer product normally includes from about 78 to 85% by weight total hydrolyzed grain protein therein, and more preferably from about 80 to 83% by weight thereof. The product moreover has a pH of from about 3–6, more preferably from about 4–5; a solids content of from about 15–25% by weight, more preferably from about 17–22% by weight; and up to about 2.5% by weight ash therein, more preferably up to about 1.5% by weight ash.

The aqueous liquid hydrolyzed grain protein ingredient should contain from about 14 to 20% by weight protein therein, more preferably from about 16 to 19% by weight. The initially solid hydrolyzed grain protein ingredient should have a protein content of from about 90 to 95% by weight, more preferably from about 91 to 94% by weight. The initially solid hydrolyzed grain protein ingredient should be present in the aqueous liquid hydrolyzed grain protein ingredient at a level of from about 1–10% by weight, more preferably from about 2–6% by weight.

In terms of foaming power, the products of the invention should preferably exhibit an initial shaker foam test height of at least about 140 ml, and a final shaker foam test height which is at least about 70% of the initial shaker foam test height. Furthermore, the initially solid ingredient should preferably be at least 95% (more preferably at least about 98%) solubilized in the liquid ingredient.

In preparative procedures, the liquid ingredient is placed in a mixer such as a vortex mixer, and the initially solid ingredient is slowly added during vortex mixing. Thereafter, the mixing is continued for a period of from about 1–12 hours, more preferably from about 2–4 hours. Incorporation of the solid ingredient into the liquid ingredient can be done most readily at ambient temperature, although the addition can be made at temperatures ranging from about 20–75° C. Normally, the liquid is agitated using a mixer operating at from about 300–2000 rpm.

The foamer products of the invention can be used in a wide variety of products, particularly personal care products such as those selected from the group consisting of bubble baths, hair shampoos and shampoo conditioners, hair styling gels, hair conditioners, hair reparatives, sunscreens, shaving creams, and bath and shower gels. Generally, the foamer products are used at variable levels depending upon the type of product in question, although the range of use typically is from about 3 to 10% by weight, based upon the total weight of the personal care product taken as 100% by weight.

DETAILED DESCRIPTION OF THE PREFERRED EMBODIMENT

The following examples set forth preferred methods for production of the liquid foamer products of the invention. It is to be understood, however, that these examples are provided by way of illustration and nothing therein should be taken as a limitation upon the overall scope of the invention.

EXAMPLE 1

Production of Aqueous Liquid Hydrolyzed Grain Protein

In the first step, 500 gallons of soft water (140° F.) was transferred into a homomixer tank, followed by agitation and the addition of 22 pounds of 50% sodium hydroxide solution. Next, 2,500 pounds of wheat gluten is added, with continued mixing for 20 minutes. Fifteen pounds of protease enzyme (Alcalase) is then added with stirring for 120 minutes while maintaining the pH of the mixture between 7.5–8.0 using 50% sodium hydroxide solution. An additional 15 pounds of the Alcalase protease enzyme is then added with stirring for an additional 120 minutes.

The pH of the enzyme-treated mixture is then adjusted to 6.4–6.6 using lactic acid, followed by the addition of 3 pounds of another protease enzyme (Dual Protease) and 10 pounds of a third protease enzyme (Neutrase). The mixture is then stirred for 60 minutes and the pH is lowered to 4.1–4.3 using lactic acid. Next, the slurry is heated to 175° F. to deactivate the protease enzymes, followed by filtration using a rotary vacuum filter.

The filtrate is then clarified through a Zeta Pak housing equipped with an H60 filter. Thereupon, the clarified filtrate is processed in a nano filtration membrane to generate a retentate fraction and a permeate fraction. The retentate fraction is collected and concentrated to a level of about 23–27% by weight solids by nano filtration. Preservatives (1% LiquaPar PE and 0.1% Versene) were added and the slurry chilled to 34–35° F. The chilled slurry was then filtered using the Zeta Pak housing and H60 filter. This filtrate was then aged under ambient conditions for one week, and the aged material was again filtered using the Zeta Pak housing equipped with an H90 filter. This filtrate is collected as the desired liquid aqueous hydrolyzed grain protein product.

EXAMPLE 2

Production of Initially Solid Hydrolyzed Grain Protein

In the first step, 310 gallons of soft water was transferred to a reaction tank. The tank agitator was turned on, and 4.5 liters (11.5 lbs.) of lactic acid was added. 1200 lbs. of wet gluten was then added and the addition line was flushed with 30 gallons of soft water. The slurry was then mixed using the agitator for five minutes. Next, 600 lbs. of wet gluten was added with addition line flushing using 30 gallons of soft water. A further agitation mixing was carried for five minutes. A still further 600 lbs. of wet gluten was then added, followed by flushing using 90 gallons of soft water.

1.5 lbs. of protease enzyme (Liquipanol T-100) was added to the slurry, by mixing for 60 minutes. 0.7 lbs. of sodium benzoate and 1.4 lbs. of potassium sorbate were next added, followed by mixing for 10 minutes. The slurry was then centrifuged, with collection of the centrifugate and disposal of ejected solids. The centrifugate was heated to 205–210° F. by direct steam injection in order to deactivate the protease enzyme. The heated dispersion was then spray dried and collected.

EXAMPLE 3

Production of Liquid Foamer Product

Initially, 600 gallons (5400 lbs.) of the aqueous hydrolyzed grain protein product from Example 1 was transferred to a mixing tank. The agitator was turned on and 270 lbs. of the initially solid hydrolyzed grain protein from Example 2 was slowly added. The agitation was continued for 3 hours in order to completely disperse the initially solid product.

An additional 185 gallons (1665 lbs.) of the Example 1 liquid was next added to the mixing tank with agitation for 30 minutes. 198 gallons (1649 lbs.) of water containing 16.5 lbs. of preservative (LiquaPar PE) was added to the mixing tank with an additional 30 minutes agitation. The dispersion was filtered using a Zeta Pak housing equipped with an H60 filter, and the liquid foamer product was collected.

EXAMPLE 4

Shaker Foam Testing

In this example a series of shaker foam tests were carried out to determine the suitability of foamer products for use in personal care products such as shampoos and the like. In each test, a 250 ml graduated cylinder (graduated in 10 ml increments) with a rubber stopper was employed. A 10% test solution was prepared using 25° C. water in a manner to avoid bubble formation. 100 grams of the 10% test solution was slowly poured into the graduated cylinder along the cylinder side so as to avoid as much bubble formation as possible. The cylinder was then stoppered and inverted 10 times from an upright to a 360° position. Immediately after the last inversion the cylinder was placed on a flat level surface and initial foam height was recorded, along with initial water height. The cylinder was allowed to sit undisturbed for 15 minutes and a final foam height and final water height was recorded. Foam quality (smooth, rough, even) and foam shape (round, honeycomb, small, thin-weak) were also recorded. This test was repeated and the results were recorded. As used herein, "initial shaker foam test height" and "final shaker foam test height" refer to the initial and final foam heights determined by way of this shaker foam test.

In one series of shaker foam tests (Table 1) using the liquid product of Example 1, 1%, 3%, 5%, and 7% solutions in water were prepared and tested. The following results were recorded:

TABLE 1

| % Concentration | 1% | 3% | 5% | 7% |
| --- | --- | --- | --- | --- |
| Initial Foam Height (ml) | 100 (no foam) | 102 | 104 | 110 |
| Final Foam Height (ml) | 100 (no foam) | 100 | 100 | 100 |
| Initial Water Height (ml) | 100 | 100 | 100 | 100 |
| Final Water Height (ml) | 100 | 100 | 100 | 100 |
| Foam Quality | No foam | No foam | No foam | No foam |
| Foam Shape | No foam | No foam | No foam | No foam |

In a second test (Table 2), the initially solid product of Example 2 was tested. In this case, 1%, 3%, 5%, and 7% aqueous solutions in water were prepared and tested, giving the following results:

TABLE 2

| % Concentration | 1% | 3% | 5% | 7% |
| --- | --- | --- | --- | --- |
| Initial Foam Height (ml) | 125 | 150 | 170 | 165 |
| Final Foam Height (ml) | 105 | 105 | 105 | 105 |
| Initial Water Height (ml) | 100 | 100 | 90 | 90 |
| Final Water Height (ml) | 100 | 100 | 100 | 100 |
| Foam Quality | Smooth, not strong | Smooth, unstable | Smooth, not strong | Smooth, not strong |
| Foam Shape | Round, unstable, off-white | Round, small, unclear | Round, unstable, off-white | Round, unstable |

These tests also demonstrated that quantities of the initially solid powder settled to the bottom of the cylinder during the settling period, confirming that the product was difficult to solubilize. Also, these tests were characterized by hazy, unclear solutions.

In another test (Table 3), the liquid foamer product described in Example 3 was tested, using 10% solutions in water, which had 1%, 3%, 5% and 7% by weight content of the initially solid Example 2 product therein. The following results were recorded:

TABLE 3

| % Concentration of Solid Product | 1% | 3% | 5% | 7% |
|---|---|---|---|---|
| Initial Foam Height (ml) | 125 | 160 | 175 | 175 |
| Final Foam Height (ml) | 104 | 112 | 120 | 105 |
| Initial Water Height (ml) | 98 | 92 | 90 | 90 |
| Final Water Height (ml) | 100 | 100 | 100 | 100 |
| Foam Quality | Smooth, not strong | Smooth, even, strong, stable | Smooth, strong, stable | Smooth, initially strong, breaks after 5 minutes |
| Foam Shape | Round, unstable | Round, honeycomb | Round, honeycomb, stable, snow white | Round, honeycomb |

These products in accordance with the invention generally gave much superior foams, particularly at the preferred usage levels of from about 2–6% by weight of the initially solid product therein.

EXAMPLE 5

Personal Product Formulations Including Liquid Foamer Product

A series of exemplary personal products were formulated using the liquid foamer product of the invention (Tables 4–6).

TABLE 4

Bubble Bath

| Ingredients | Parts |
|---|---|
| Distilled Water | Adjust |
| Disodium EDTA | 0.05 |
| Ammonium Laureth Sulfate | 20.00 |
| Disodium Laureth Sulfosuccinate | 5.00 |
| Propylene Glycol | 1.00 |
| Liquid Foamer Product (Example 3) | 10.00 |
| Aqueous Liquid Hydrolyzed Grain Protein (Example 1) | 5.00 |
| Cocamide DEA | 3.00 |
| Chamomille Extract | .50 |
| Calendula Extract | .50 |

Mix all ingredients in order in a suitable tank. Adjust pH (5.5–6.5) with 25% citric acid, add fragrance and color as desired, adjust viscosity with 25% sodium chloride.

TABLE 5

Ultra Foamy Children's Bubble Bath

| Ingredients | Parts |
|---|---|
| Distilled Water | Adjust |
| Disodium EDTA | 0.05 |
| Ammonium Laureth Sulfate | 25.00 |

TABLE 5-continued

Ultra Foamy Children's Bubble Bath

| Ingredients | Parts |
|---|---|
| Disodium Laureth Sulfosuccinate | 20.00 |
| Propylene Glycol | 1.00 |
| Liquid Foamer Product (Example 3) | 18.00 |
| Quaternized hydroxypropyl triammonium | 5.00 |
| Quaternized hydrolyzed wheat protein | 5.00 |
| Cocamide DEA | 1.00 |
| Chamomille Extract (Active Organic) | .50 |
| Calendula Extract (Active Organic) | .50 |
| Preservative | QS |
| Citric Acid | QS |
| Fragrance | QS |
| Sodium Chloride | QS |

Mix all of Part A ingredients in order in a suitable tank. Adjust pH (5.5–6.5) with 25% citric acid; add fragrance and color as desired, adjust viscosity with 25% sodium chloride.

TABLE 6

Conditioning Shampoo

| Ingredients | Parts |
|---|---|
| Distilled Water | Adjust |
| Versene NA2 | 0.05 |
| Propylene Glycol Sulfate | 0.50 |
| Stepanol WAC | 10.00 |
| Stepanol CS-230 | 10.00 |
| Mackamide C | 10.00 |
| Hydrolyzed Grain Protein (Example 1) | 5.00 |
| Liquid Foamer Product (Example 3) | 3.00 |
| Chamomille Extract | 0.05 |
| Aloe Vera Extract | 0.03 |
| Preservative | QS |
| Fragrance | QS |

In a suitable primary tank meter out required amount of distilled water. Add remaining ingredients in order with good mixing. Add Parts B and C and adjust pH to 5.5–6.5 with 25% citric acid. Adjust viscosity with 10% NaCl.

What is claimed is:

1. A foamer product comprising enzymatically hydrolyzed wheat gluten protein dispersed in aqueous liquid and having a solids content of from about 15–25% by weight and up to about 2.5% by weight ash therein, said foamer product exhibiting an initial shaker foam test height of at least about 140 ml, and a final shaker foam test height which is at least about 70% of said initial shaker foam test height.

2. The product of claim 1, said product containing from about 78 to 85% by weight total hydrolyzed grain protein therein.

3. The product of claim 2, said foamer product containing from about 80 to 83% by weight total hydrolyzed grain protein therein.

4. The product of claim 1, said product having a pH of from about 3–6.

5. The product of claim 4, said product having a pH of from about 4–5.

6. The product of claim 1, said product having a solids content of from about 17–22% by weight.

7. The product of claim 1, said product having up to about 1.5% by weight ash therein.

8. The product of claim 1, said product comprising a quantity of aqueous liquid hydrolyzed grain protein and an amount of initially solid hydrolyzed grain protein solubilized in said liquid hydrolyzed grain protein, said hydrolyzed grain protein containing from about 14–20% by weight protein therein.

9. The product of claim 8, said liquid hydrolyzed grain protein containing from about 16 to 19% by weight protein therein.

10. The product of claim 8, said initially solid hydrolyzed grain protein being present at a level of from about 1–10% by weight.

11. The product of claim 10, said initially solid hydrolyzed grain protein being present at a level of from about 2–6% by weight.

12. The product of claim 1, said amount of said initially solid hydrolyzed grain protein being at least about 95% solubilized in said aqueous liquid hydrolyzed grain protein.

13. A method of preparing foamer product comprising the steps of:

providing a quantity of enzymatically hydrolyzed wheat gluten protein dispersed in aqueous liquid; and solubilizing in said aqueous liquid an amount up to about 10% by weight of an initially solid, previously hydrolyzed wheat gluten protein to form said products, wherein said product has a solids content of from about 15–25% by weight and up to about 2.5% by weight ash therein, and exhibits an initial shaker foam test height of at least about 140 ml, and a final shaker foam test height which is at least about 70% of said initial shaker foam test height.

14. The method of claim 13, said product containing from about 78 to 85% by weight total hydrolyzed grain protein therein.

15. The method of claim 14, said product containing from about 80 to 83% by weight hydrolyzed grain protein therein.

16. The method of claim 13, said product having a pH of from about 3–6.

17. The method of claim 16, said product having a pH of from about 4–5.

18. The method of claim 13, said product having a solids content of from about 17–22% by weight.

19. The method of claim 13, said product having up to about 1.5% by weight ash therein.

20. The method of claim 13, said liquid hydrolyzed grain protein containing from about 14 to 20% by weight protein therein.

21. The method of claim 20, said liquid hydrolyzed grain protein containing from about 16 to 19% by weight protein therein.

22. The method of claim 13, said initially solid hydrolyzed grain protein being present at a level of from about 1–8% by weight.

23. The method of claim 22, said initially solid hydrolyzed grain protein being present at a level of from about 2–6% by weight.

24. The method of claim 13, said amount of said initially solid hydrolyzed grain protein being at least about 95% solubilized in said aqueous liquid hydrolyzed grain protein.

25. A personal care product selected from the group consisting of bubble baths, hair shampoos and shampoo conditioners, hair styling gels, hair conditioners, hair reparatives, sunscreens, shaving creams, and bath and shower gels which includes therein a quantity of the foamer product of claim 1.

26. The personal care product of claim 25, said foamer product being present at a level of from about 3 to 10% by weight in the personal care product.

* * * * *